United States Patent [19]

DeBonville

[11] Patent Number: 5,096,818
[45] Date of Patent: Mar. 17, 1992

[54] NUCLEIC ACID SEPARATION METHOD

[75] Inventor: David A. DeBonville, Beverly, Mass.

[73] Assignee: AutoGen Instruments, Inc., Beverly, Mass.

[21] Appl. No.: 534,025

[22] Filed: Jun. 4, 1990

[51] Int. Cl.$^5$ .................... C12P 19/34; C12N 1/06
[52] U.S. Cl. .................... 435/91; 435/172.1; 435/172.3; 435/259; 536/27; 935/19; 935/20; 935/21
[58] Field of Search .................... 435/91, 172.1, 172.3, 435/259; 935/19-21; 536/27

[56] References Cited

U.S. PATENT DOCUMENTS

| | | | |
|---|---|---|---|
| 4,283,489 | 8/1981 | Goodman et al. | 935/21 |
| 4,649,119 | 3/1987 | Sinskey et al. | 435/172.3 |
| 4,752,574 | 6/1988 | Hershberger et al. | 435/172.3 |
| 4,755,464 | 7/1988 | MacPhee et al. | 935/19 |
| 4,833,239 | 5/1989 | DeBonville et al. | 536/27 |
| 4,843,012 | 6/1989 | DeBonville et al. | 435/259 |
| 4,855,237 | 8/1989 | Morinaga et al. | 435/173.3 |
| 4,900,677 | 2/1990 | Hewitt | 435/259 |
| 4,921,805 | 5/1990 | Gebeyehu et al. | 935/19 |
| 4,921,952 | 5/1990 | Longmire et al. | 536/27 |
| 4,935,342 | 6/1990 | Seligson et al. | 935/19 |

FOREIGN PATENT DOCUMENTS 0276692 3/1990 Fed. Rep. of Germany ...... 435/259

Primary Examiner—Herbert J. Lilling
Attorney, Agent, or Firm—Iandiorio & Dingman

[57] ABSTRACT

An improved method for isolating and purifying nucleic acid from cell culture media contemplating adding to resuspended cell solutions a lysing solution and neutralizing/deproteinating agent without mechanical mixing, followed by centrifugation to partially pellet cellular debris, mixing the solution to complete the reaction, and additional centrifugation to fully pellet the debris.

8 Claims, No Drawings

NUCLEIC ACID SEPARATION METHOD

FIELD OF INVENTION

This invention relates to an improved nucleic acid separation technique which is particularly suited for automated separation procedures.

BACKGROUND OF INVENTION

The isolation and analysis of nucleic acids from various sources is a commonly performed procedure in genetic and recombinant DNA research. As the primary genetic elements, nucleic acids will exist in various forms depending on the biological source: Mammalian sources (such as blood) contain large, double-stranded, filamentous DNA (20-500 million bases); viruses (HIV or Epstein-Barr) can contain single- or double-stranded DNA or RNA, filamentous or closed-circular in structure (10-200 kilobases); bacteria (particularly variants of *E. coli* K-12) contain a single chromosome (4 million bases) and extra chromosomal elements, either plasmids or cosmids (2-50 kilobases), in *E. coli* these elements are all double-stranded, closed-circular DNA molecules. The procedures and chemistries commonly employed T. Maniatis et al.: *Molecular Cloning—A Laboratory Manual*, Cold Spring Harbor Laboratory (1989).

The chemistries typically involve breaking open the cells or viral particles, extracting cellular and protein contaminants, purifying and concentrating the nucleic acids and then resuspending it in small volume prior to use. Purification of plasmids or cosmids requires the additional step of separation from the bacterial chromosome prior to their use. This technique, originally described by H. C. Birnboim and J. Doly "A Rapid Alkaline Extraction Procedure for Screening Recombinant Plasmid DNA", *Nucleic Acids Research* 7:1513-1523 (1979), accomplishes this separation based on the plasmid or cosmid's capacity to resist denaturation (i.e. separation of the complementary DNA strands into their single-stranded components). Since the size of the DNA molecule influences its resistance to denaturation, and subsequent co-purification with plasmids and cosmids, it is important that the bacterial chromosome not be broken into smaller fragments during the course of the procedure. For this reason, manual protocols emphasize gentle mixing. In general, any DNA isolation procedure that will reduce the amount of shearing of chromosomal DNA is desirable.

A major contributor to the breakup of large bacterial chromosomes are the shear forces generated during the preparational procedure. When the procedures are performed manually, the undesirable high shear forces are avoided by accomplishing mixing by slowly inverting the test tubes. However, in automated separation procedures employing automatic equipment to perform some or all of the separation steps, such slow, gentle mixing by capping and inverting the test tubes is difficult and costly to accomplish.

In automated DNA separation techniques, the tube contents are typically mixed by repeated pipetting of the solution, blowing bubbles into the solution, or shaking the tubes to simulate vortexing. Each of these mixing procedures generates significant shear forces as compared to the slow-inversion manual technique. Accordingly, the automated DNA separation procedures have been characterized by low yields of plasmid or cosmid DNA of an inferior quality, at least partially due to contamination by chromosomal fragments. In addition, the automated separation procedures typically take more time than the manual methods because the mixing steps are very slow and inefficient.

SUMMARY OF INVENTION

It is therefore an object of this invention to provide an improved DNA separation procedure which increases the yield and quality of plasmid and/or cosmid DNA.

It is a further object of this invention to provide such a procedure which employs the mixing processes of automated DNA separation techniques.

It is a further object of this invention to provide such a procedure which when applied to automated separation techniques provides high quality results.

This invention results from the realization that automated DNA separation techniques can be dramatically improved by adding the lysing/denaturing and the deproteinating and/or neutralizing agent to the resuspended cells without mixing, followed by centrifuging the solution to partially pellet the cellular debris, and then mixing the solution to complete the lysing and deproteinization, followed by a second centrifugation that completely pellets the cellular debris.

DISCLOSURE OF PREFERRED EMBODIMENT

Other objects, features and advantages will occur to those skilled in the art from the following description of a preferred embodiment.

This invention may be accomplished in an improved method for isolating and purifying nucleic acid from cell culture media in which the lysing/denaturing and the deproteinating and neutralizing agent or agents are added to the resuspended cells without mechanical mixing, the resultant solution is centrifuged to partially pellet the cellular debris, and then mixed to complete the lysis/denaturization and neutralization/deproteinization before the cellular debris is finally and fully eliminated by centrifugation. As a result, the high-shear force mixing procedures available in automated DNA preparation devices may be employed to accomplish separations at least as good as those accomplished in the more laborious manual separation techniques.

In standard plasmid/cosmid isolation protocols, performed manually or automatically, the cells are pelleted by centrifugation and the nutrient broth is siphoned off and discarded. The pelleted cells are then resuspended in an isotonic buffer by vigorous mixing. A lysing-/denaturing reagent is then added to the resuspended cells, and the tube is mixed. In the manual techniques, the low-shear force, gentle mixing required to prevent the chromosomal DNA from fragmenting is accomplished by capping and gently inverting the tube one or more times to completely combine the different reagents. Incubating and mixing are typically performed at reduced temperatures (i.e. on ice) to further reduce breakup of chromosomal DNA. Mixing is complete when a very viscous solution is observed. In the automated procedures, such gentle mixing is typically not available; substituted therefor is mixing accomplished by: repeated pipetting of the solution, blowing bubbles into the solution, or shaking the tubes to simulate vortexing. However, each of these procedures provides high shear forces which tend to break the chromosomal DNA into small fragments, which are then co-purified with the plasmid or cosmid DNA, resulting in lower yields and lower quantity separations.

After the mixing, the solution is typically incubated on ice for several minutes, and then a neutralizing reagent is added, followed by further mixing as described above. The tube is then again incubated on ice for several minutes, followed by a centrifugation to completely pellet the cellular debris. The lysate is then transferred to a clean tube where the nucleic acid is precipitated with an alcohol solution, followed by a removal of the supernatant, washing of the nucleic acid, and resuspension in a buffer.

Thus, both the standard manual and automatic protocols provide two mixing steps, one after the addition of the lysing/denaturing reagent, and one more after addition of the neutralizing reagent. Accordingly, the chromosomal DNA is twice subjected to the mixing shear forces before the solution is centrifuged to pellet cellular debris, and there is a great chance of fragmentation of at least some of the chromosomal DNA.

In contrast, in the improved method of this invention, the solution containing the chromosomal DNA is subject only to a single mixing step before the debris is fully pelleted by centrifugation. In addition, this mixing step is accomplished only after the tube has been centrifuged a first time to partially pellet the cellular debris, thereby removing at least some of the bacterial chromosomal DNA with the partially precipitated cellular debris, reducing susceptibility of the chromosomal DNA to the excessive shear forces generated by the automated procedure mixing procedures—repeated pipetting, bubble blowing, or vortexing.

EXAMPLE I

Plasmid/Cosmid Isolation Protocol

The separation method of this invention has been used in isolating plasmid/cosmid DNA as follows:

The *E. coli* cells were pelleted by centrifugation at 4,000 rpm for two minutes. The nutrient broth was then removed from the tubes and discarded to waste by pipetting. An isotonic buffer was then added to the pelleted cells and the cells resuspended in the buffer by pipet mixing the tube contents—in other words, by repeated pipetting of the contents.

A lysing/denaturing reagent was then added to the resuspended cell sample. The mixing action on reagent addition partially mixes the reagent with the cell sample to partially react the chemical components; the tube is not mechanically mixed at this time. There is no incubation on ice following the addition of the lysing/denaturing reagent.

The neutralizing and deproteinating reagent was then added to the tube. Again, the turbulence generated by addition of the reagent was the only tube mixing provided. This partial mixing results in a partial reaction of the chemical components. As before, there was no incubation step following the addition of the neutralizing reagent.

The tube was then centrifuged at 9,000 rpm for two minutes to partially pellet the cellular debris. The tube contents were mixed by repeated pipetting. The tube was then recentrifuged again at 9,000 rpm for two minutes to fully pellet the cellular debris. The procedure then proceeded with the transfer of the lysate to a clean tube, followed by the nucleic acid precipitation, washing and resuspension as described above. The result was plasmid/cosmid yield and quality at least as good as that of the manual procedure employing the two gentle mixing steps employing process steps suited for use in automated separation devices.

EXAMPLE II

Genomic DNA Isolation of Blood

High molecular weight DNA is typically manually separated from tissue sources by adding an enzymatic/lysing reagent to cells resuspended in an isotonic buffer, and gently mixing the contents, followed by incubation from two to sixteen hours at 37° C. to 55° C. Protein extracting reagent is then added to the tube and the tube is again mixed gently by inversion, followed by centrifugation to fully pellet the cellular debris, and then transfer of the lysate, followed by a repeat of the protein extraction and centrifugation steps, a second lysate transfer, and then the standard nucleic acid precipitation and resuspension.

The method of this invention has been applied to isolating genomic DNA from blood samples by adding the lysing reagent to disrupt the resuspended cells without mechanically mixing the tube contents; the only mixing is provided by the force of reagent addition into the tube. The two to sixteen hour incubation step was also not necessary in the procedure, as no enzymatic component was used.

A neutralizing and deproteinating reagent was then added to the tube. Again, the tube contents were not mixed—the force of reagent addition was the only mixing provided. After addition of the reagent, the tube was spun at 9,000 rpm for two minutes to partially pellet the cellular debris, followed by a high-shear force mixing of the tube contents by repeated pipetting. It is believed that the partial pelleting before mixing reduces shear forces on the DNA caused by the presence of partially reacted cellular debris, thus providing superior results even with the high-shear force mixing. After the mixing step, the tube was again spun at 9,000 rpm for two minutes to fully pellet the cellular debris, followed by a transfer of the lysate and precipitation and suspension of the nucleic acids as before.

Accordingly, when applied to isolation of genomic DNA from tissue samples, the method of this invention replaces the three mixing steps of the manual method—once after addition of the lysing reagent and once after each of the two additions of the protein extracting reagent—with a single mixing step provided after the cellular debris is partially pelleted. In addition, the repeated performance of the protein extraction step of the manual procedures is obviated by the addition of the lysing reagent followed by the neutralizing reagent and partial pelleting of the cellular debris before mixing of the tube contents.

The procedures of this invention thus accomplish substantially the same results as the manual isolation techniques using automated equipment, thereby saving substantial technician's time. In addition, the method of this invention allows the separations to be performed on an automated machine with quality levels as good as those provided in the manual methods without the variability of results inherent in the manual separation techniques.

Other embodiments will occur to those skilled in the art and are within the following claims:

What is claimed is:

1. An improved method for isolating and purifying nucleic acid from cell culture media of the type in which:

(a) cells in the culture are concentrated apart from major contaminants in the media and resuspended in buffer in a tube;
(b) the cells are lysed in the presence of a lysing solution;
(c) the resulting solution is neutralized and deproteinated in the presence of a neutralizing and deproteinating agent; and
(d) cellular debris is eliminated;
wherein the improvement comprises:
(e) adding to the resuspended cells the lysing solution and the neutralizing/deproteinating agent without mechanical mixing of the tube contents by repeated pipetting, bubble blowing or shaking the tube, to at least partially accomplish the lysing, neutralization and deproteination;
(f) centrifuging the tube to partially pellet the cellular debris (g) mechanically mixing the solution after partial pelleting; and
(h) centrifuging a second time to fully pellet and eliminate cellular debris.

2. The method of claim 1 in which said mechanical mixing includes repeated pipetting of the solution.

3. The method of claim 1 in which said mechanical mixing includes blowing bubbles into the solution.

4. The method of claim 1 in which said mechanical mixing includes vortexing the solution.

5. An improved method for isolating and purifying nucleic acid from cell culture media of the type in which:
(a) cells in the culture are concentrated apart from major contaminants in the media and resuspended in a buffer in a tube;
(b) the cells are lysed in the presence of a lysing solution; and
(c) the resulting solution is deproteinated in the presence of a deproteinating agent;
wherein the improvement comprises:
(d) adding the lysing solution and the deproteinating agent to the resuspended cells without mechanical mixing of the tube contents by repeated pipetting, bubble blowing or shaking the tube, to at least partially accomplish the lysing neutralization and deproteination;
(e) centrifuging the tube to partially pellet the cellular debris (f) mechanically mixing the solution after partial pelleting; and
(g) centrifuging a second time to fully pellet and eliminate cellular debris.

6. The method of claim 5 in which said mechanical mixing includes repeated pipetting of the solution.

7. The method of claim 5 in which said mechanical mixing includes blowing bubbles into the solution.

8. The method of claim 5 in which said mechanical mixing includes vortexing the solution.

* * * * *